United States Patent
Amelia et al.

(10) Patent No.: US 9,789,343 B2
(45) Date of Patent: Oct. 17, 2017

(54) ACCESSORY HOLDER FOR PARTICLE BEAM APPARATUS

(71) Applicant: ION BEAM APPLICATIONS S.A., Louvain-la-Neuve (BE)

(72) Inventors: Jean-Claude Amelia, Erquelinnes (BE); Thomas Colmant, Braives (BE); Sven De Roeck, Brussels (BE)

(73) Assignee: Ion Beam Applications S.A., Louvain-la-Neuve (BE)

( * ) Notice: Subject to any disclaimer, the term of this patent is extended or adjusted under 35 U.S.C. 154(b) by 0 days.

(21) Appl. No.: 14/779,790

(22) PCT Filed: Mar. 26, 2014

(86) PCT No.: PCT/EP2014/056044
§ 371 (c)(1),
(2) Date: Sep. 24, 2015

(87) PCT Pub. No.: WO2014/154740
PCT Pub. Date: Oct. 2, 2014

(65) Prior Publication Data
US 2016/0045769 A1    Feb. 18, 2016

(30) Foreign Application Priority Data
Mar. 26, 2013  (EP) .................................... 13161202

(51) Int. Cl.
*A61N 5/10*    (2006.01)

(52) U.S. Cl.
CPC ......... *A61N 5/1083* (2013.01); *A61N 5/1042* (2013.01); *A61N 5/1043* (2013.01);
(Continued)

(58) Field of Classification Search
USPC ..................................................... 250/492.1
See application file for complete search history.

(56) References Cited

U.S. PATENT DOCUMENTS

| | | | |
|---|---|---|---|
| 6,034,377 A * | 3/2000 | Pu ........................ | A61N 5/1043 250/398 |
| 7,402,822 B2 * | 7/2008 | Guertin .................... | A61N 5/10 250/492.3 |

(Continued)

FOREIGN PATENT DOCUMENTS

| JP | 2010/017365 | 1/2010 |
|----|-------------|--------|
| WO | WO 2009/070173 | 6/2009 |
| WO | WO 2013/011583 | 6/2011 |

OTHER PUBLICATIONS

International Search Report for International Patent Application No. PCT/EP2014/056044, filed Mar. 26, 2014. (3 pgs).

*Primary Examiner* — Phillip A Johnston
(74) *Attorney, Agent, or Firm* — Finnegan, Henderson, Farabow, Garrett & Dunner LLP (57) ABSTRACT

The present disclosure relates to an accessory holder attachable to or integrated in the nozzle of an apparatus for particle beam irradiation treatment. The accessory may be an aperture piece, a range shifter or any other element that can be placed in the beam path between the outer end of the nozzle and the irradiated target. The accessory holder may be equipped with first displacement means for moving the accessory away from or towards the nozzle, thereby moving the accessory forwards and backwards in the direction of the beam and second displacement means for moving the accessory into or out of the beam path. Measurements or treatment steps may be performed with and without the accessory in the beam path, without interrupting the treatment.

17 Claims, 7 Drawing Sheets

(52) U.S. Cl.
CPC .... *A61N 5/1077* (2013.01); *A61N 2005/1074* (2013.01); *A61N 2005/1087* (2013.01); *A61N 2005/1095* (2013.01)

(56) References Cited

U.S. PATENT DOCUMENTS

| | | | |
|---|---|---|---|
| 2005/0087700 A1* | 4/2005 | Tadokoro | A61N 5/1048 250/492.21 |
| 2006/0017015 A1 | 1/2006 | Sliski et al. | |
| 2010/0301228 A1 | 12/2010 | Pu | |
| 2011/0218429 A1 | 9/2011 | Harada et al. | |
| 2012/0316378 A1 | 12/2012 | Torikai et al. | |

\* cited by examiner

ACCESSORY HOLDER FOR PARTICLE BEAM APPARATUS

FIELD OF THE INVENTION

The invention is related to installations for particle beam treatment, such as proton therapy, wherein a tumor is irradiated with a proton beam. The invention is particularly related to an accessory holder attachable to the nozzle of a particle beam apparatus.

STATE OF THE ART

In particle beam treatment, a number of irradiation techniques are known today. In Pencil Beam scanning (PBS), a proton beam produced by a radiation source such as a cyclotron, is targeted at subsequent points within subsequent layers of the treated tumor. Each layer of the tumor is thereby 'scanned' (also referred to as 'painted') by a beam, the beam intensity for points in each layer being controlled so that the prescribed dose is delivered at the point in question. This technique represents an advance over the single or double scattering technique, wherein a scattered beam is shaped by a patient specific collimator, so that it corresponds to the shape of the treated tumor.

Even though PBS does not require the expensive and heavy patient specific collimator, specific accessories may need to be placed in the path of the beam between the nozzle and the target before or during a scanning treatment, such as a ridge filter, a range compensator or range shifter, or an aperture for improving the lateral penumbra or for sparing organs at risk that are situated close to the treated tumor. These accessories need to be mounted and removed manually, which leads to a considerable loss of time and efficiency of the treatment installation.

Regardless of the irradiation technique used, means for holding accessories in the path of a beam between the nozzle and the target, with the possibility of approaching the target at a close distance, are generally lacking flexibility of use, both in terms of the available movements and their control and automation.

SUMMARY OF THE INVENTION

The present invention is related to an accessory holder attachable to or integrated in the nozzle of an apparatus for particle beam irradiation treatment. The accessory may be an aperture piece, a range shifter or any other element that can be placed in the beam path between the outer end of the nozzle and the irradiated target. The accessory holder is equipped with first displacement means for moving the accessory away from or towards the nozzle, thereby moving the accessory forwards and backwards in the direction of the beam and second displacement means for moving the accessory into or out of the beam path. Measurements or treatment steps can thus be performed with and without the accessory in the beam path, without interrupting the treatment. According to a preferred embodiment, the first displacement means comprises an eccentrically placed axle equipped with actuator arms which are designed to actuate a linear movement of support rods which support the second displacement means, the latter comprising a slidable drawer into which the accessory can be inserted.

The invention is related to an accessory holder, a particle beam irradiation apparatus and a method as disclosed in the appended claims.

The invention is thus related to an accessory holder for a particle beam treatment apparatus comprising a nozzle for delivering a beam to a target, said holder being connectable to or integrated in said nozzle, the holder comprising:

An accessory interface configured for releasably receiving and holding an accessory, First displacement means for moving said accessory interface in a first direction, so that an accessory, while being held by said interface, may be moved away from or towards the nozzle in the direction of a beam produced by said apparatus, Second displacement means for moving said accessory interface in a second direction, so that an accessory, while being held by said interface, may be moved into or out of the path of a beam produced by said apparatus.

According to a first embodiment, said first displacement means comprises a first movable portion configured to move in said first direction with respect to the nozzle, and wherein the second displacement means comprises a second movable portion configured to move in said second direction with respect to said first movable portion, and wherein the second movable portion comprises said accessory interface.

According to a second embodiment, said second displacement means comprises a second movable portion, configured to move in said second direction with respect to the nozzle and wherein the first displacement means comprises a first movable portion configured to move in said first direction with respect to said second movable portion, and wherein the first movable portion comprises said accessory interface.

According to an embodiment, the first displacement means does not comprise an expansion and contraction section having a bellows shape.

Preferably said movement in the second direction, into or out of the path of the beam, is a linear translational movement such as the sliding of a tray that can be moved into or out of the beam path.

In an accessory holder according to the first embodiment, the first displacement means may further comprise a rotatable axle provided with actuator arms configured to move the first movable portion along said first direction away from or towards the nozzle.

Further in an accessory holder according to the first embodiment, the second movable portion may comprise a slidable drawer configured to slide back and forth in said second direction, said drawer comprising said interface to receive and secure an accessory.

An accessory holder according to the invention may comprise a base portion connectable to said nozzle, with said first or second displacement means being mounted on said base portion.

According to an embodiment of the accessory holder comprising a base portion connectable to said nozzle, with said first or second displacement means being mounted on said base portion, said first displacement means further comprises support pieces and support rods attached at one end to said support pieces and supporting the first movable portion at the other end, the base portion comprising guide holes into which said rods are inserted, and wherein said arms are provided with elongate openings, configured to slidably receive cylindrical ends of said support pieces, so that rotation of said arms actuates a linear movement of said support rods In an accessory holder according a preferred embodiment of the invention, the first and second displacement means are motorized and actuatable from a distance, i.e. without requiring manual manipulation of the movable portions of the displacement means. The first and/or second displacement means may comprise electrical and/or pneumatic drive means.

According to an embodiment, said first direction is the direction of a first linear path, and the wherein the second direction is the direction of a second linear path perpendicular to the first linear path.

The invention is equally related to a particle beam apparatus comprising an irradiation source and a nozzle, with an accessory holder according to the invention mounted on or incorporated in said nozzle. Said apparatus may comprise a particle beam scanning device for scanning a particle beam over a target.

According to an embodiment of the particle beam apparatus according to the invention, the apparatus comprises a snout attachable to said accessory holder and whereby said snout is further configured for holding one or more accessories such as an aperture, a range compensator, a ridge filter or a range shifter.

The invention is equally related to a method for positioning an accessory in a particle beam treatment apparatus comprising a nozzle for delivering a beam to a target and an accessory holder connected to or integrated in said nozzle, said holder comprising:

An accessory interface configured for releasably receiving and holding an accessory, First displacement means for moving said accessory interface in a first direction, so that an accessory, while being held by said interface, may be moved away from or towards the nozzle in the direction of a beam produced by said apparatus, Second displacement means for moving said accessory interface in a second direction, so that an accessory, while being held by said interface, may be moved into or out of the path of a beam produced by said apparatus, the method comprising the steps of:

inserting and securing the accessory in said accessory interface, moving the accessory along the first and second direction or vice versa, thereby bringing the accessory in a predefined position with respect to said target, wherein the accessory remains inserted and secured in said interface during said movements.

In the method of the invention, said movements may be actuated by automated drive means controlled by an operator, i.e. the movements are motorized and actuated from a distance. No manual manipulations are required during said movements.

In the method of the invention, said accessory may be an aperture piece or a range shifter or a ridge filter for use with a Pencil Beam Scanning nozzle or wherein said accessory is a holding means holding such an aperture piece, range shifter or ridge filter.

DETAILED DESCRIPTION OF THE INVENTION

Figure 1:
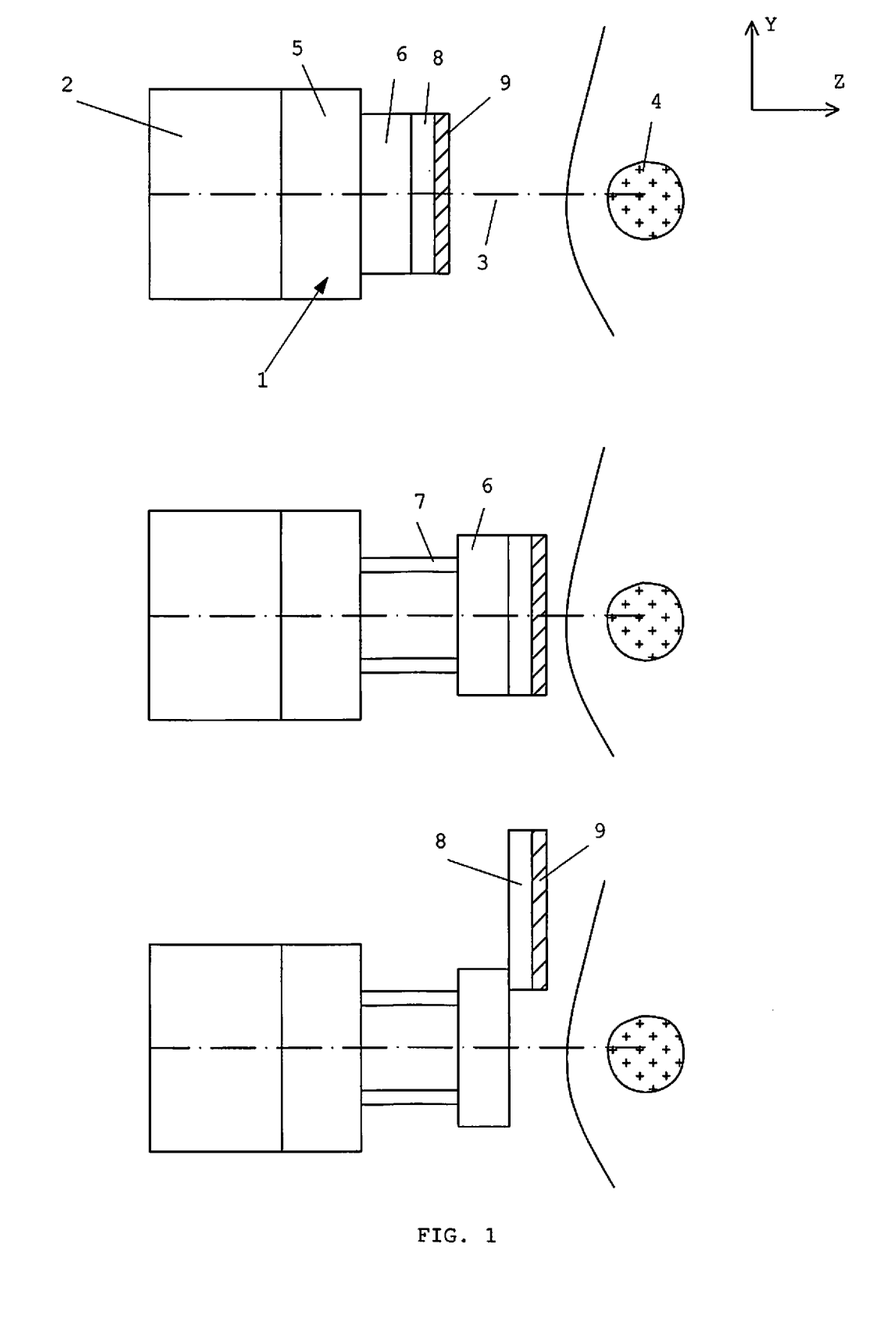
FIG. 1 illustrates the working principle of an accessory holder according to a first embodiment.
Figure 2:
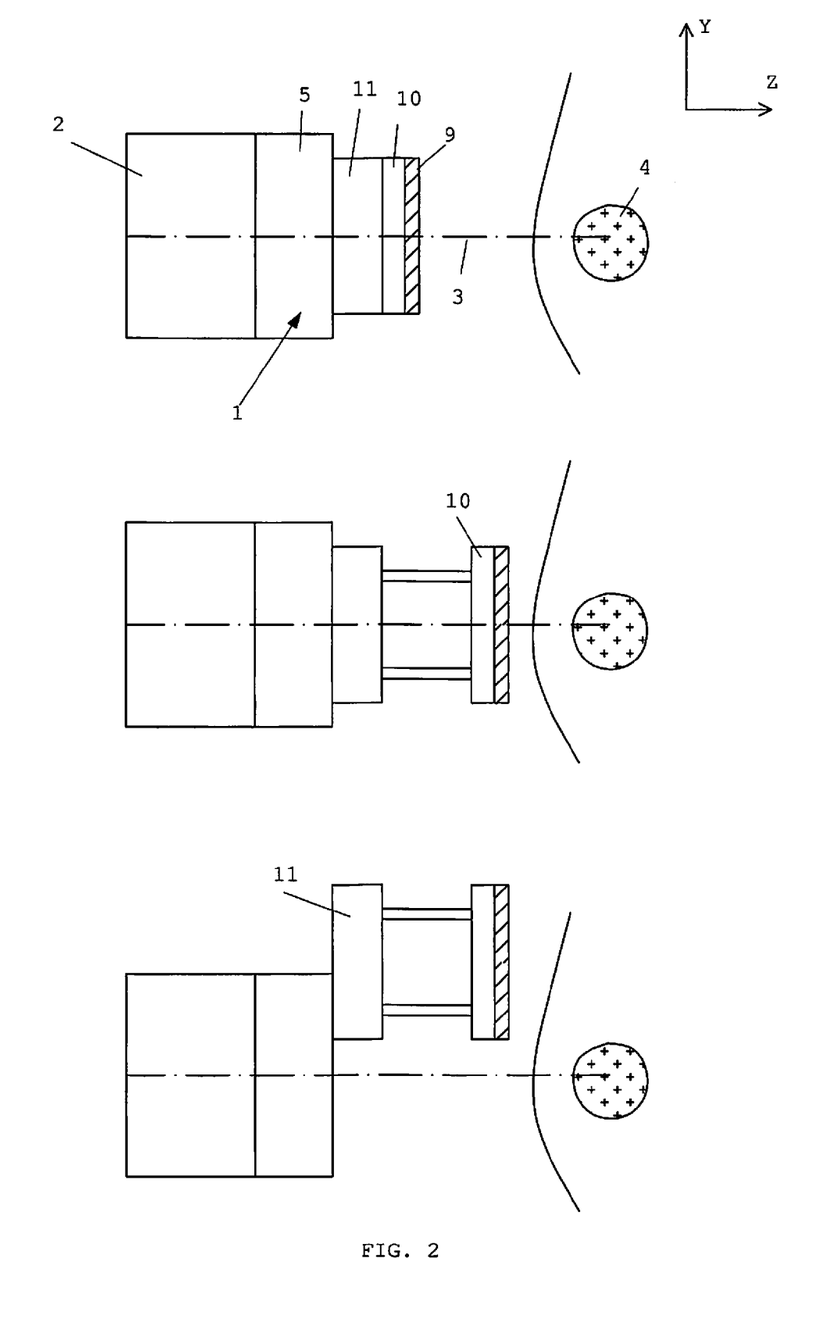
FIG. 2 illustrates the working principle of an accessory holder according to a second embodiment.

FIGS. 1 and 2 illustrate the basic structure of an accessory holder according to the invention. In each case, the holder 1 is attachable to the nozzle 2 of a particle beam installation. In this detailed description the nozzle is described as a Pencil Beam Scanning nozzle, even though the invention is not limited to this type of irradiation nozzle. In the context of the present description, the term nozzle refers to the last part in the sequence of parts, starting with the beam source, required to produce a scanning beam 3, directed at a target, such as a patient tumour 4. The nozzle is usually the part that comprises the dosimetry device for measuring the delivered dose. In some particle therapy configurations the nozzle comprises the scanning magnets for performing the pencil beam scanning. In other particle therapy configurations the scanning magnets for performing pencil beam scanning are installed more upstream in the beam line. For example in compact gantry systems, the scanning magnets are installed upstream of the last bending magnet and the part downstream of the last bending magnet comprising the dosimetry device can be called the nozzle.

In each of the embodiments of FIGS. 1 and 2, the accessory holder 1 comprises a base portion 5 that is attached (e.g. bolted) to the nozzle 2. The base portion is preferably releasably attached to the nozzle. Nevertheless, the accessory holder of the invention can stay attached to the nozzle during a complete treatment process, and may need to be removed only in case of repairs or maintenance of the installation. According to another embodiment, the accessory holder is fully integrated in the nozzle. There is then no separate base portion as the function of this base portion (i.e. carrying the first and second displacement means) is fulfilled by the nozzle itself. In this case, the base portion is part of the overall nozzle frame.

In the embodiment of FIG. 1, a first movable portion 6 is mounted on the base portion 5 and configured to be movable with respect to said base portion, in the Z-direction indicated in the drawing, i.e. closer to or away from the target 4. Support and/or guide elements 7 and a suitable power source (not shown) are provided for guiding and driving this movement. A second movable portion 8 is mounted on the first movable portion 6 and configured to be movable in the Y-direction, with respect to said first portion, the Y-direction being perpendicular to the Z-direction. An accessory 9 attached to the second movable portion 8 can thus be moved into and out of the beam path. Further driving means (not shown) are provided for actuating this sideways movement. The second movable portion 8 is provided with an interface (not shown) configured for receiving an accessory 9 and holding the accessory during the movements along the Z and Y-axes.

The interface can be a separate interface part attached to the movable portion 8 or it can be integrated in the movable portion 8. The interface can for example comprise a slot with a locking mechanism for inserting and removing an accessory 9 and for locking the accessory 9 to the second movable portion 8, so that during motion of the second movable portion 8, the accessory 9 remains attached to the second movable portion 8. The interface is preferably not designed to receive one particular type of accessory, but rather it is designed to receive any type of accessory that may need to be installed, such as a range shifter or an aperture. According to an advantageous embodiment, the interface comprises a rectangular receiving area provided in the movable portion (e.g. a drawer) that is configured to move into or out of the beam path, said area being delimited by side beams, into which the accessory can be inserted by sliding the accessory into said area. Locking means such as pneumatically operated locking pins are then provided for maintaining the accessory in a fixed position with respect to the moveable portion.

Therefore, held by the interface, the accessory 9 remains attached to the second movable portion 8 in any position of said first and second movable portions. In this way, the accessory can be brought closer to the target and/or into and out of the beam path without removing it from the accessory holder as such. This capability allows to perform multiple irradiation steps with and without accessories in the beam path, without interrupting the treatment.

In the embodiment of FIG. 2, the same functionalities as the embodiment of FIG. 1 are obtained, but the roles of the movable portions are reversed. A first movable portion 10 is movable in the Z-direction and provided with an interface (not shown) for receiving and holding the accessory 9. The first movable portion 10 is mounted on a second movable portion 11 and configured to move in the Z-direction with respect to said second movable portion 11. The second movable portion 11 is itself mounted on the base portion 5, and configured to be movable in the Y-direction, with respect to said base portion 5.

Both embodiments shown in FIGS. 1 and 2 are examples of how to bring the invention into practice. All of the described displacement means are motorized and actuatable from a distance, through the use of suitable drive and actuator means, such as electrical motors, pneumatic actuators or the like. The first embodiment shown in FIG. 1 is the preferred option as it allows the second movable portion 8, i.e. the portion that is slidable sideways with respect to the beam direction, to be produced in a manner that takes up a minimum of space in said beam direction, as will be illustrated in a detailed embodiment described further on. Variations on the designs of FIGS. 1 and 2 may be obtained by specific ranges for the Z and Y movements, the angle between said Z and Y-movements, or the capability of moving the accessory in multiple directions oriented at a non-zero angle with respect to the Z-direction. The second moveable portions 8 and 11 are preferably moveable by a linear translational movement, i.e. a movement along a straight line.

The Z and Y directions are examples of the 'first' and 'second' direction referred to in the claims. Another way of referring to these directions may be 'longitudinal' and 'lateral' directions. The described movements in the Z-direction are examples of movements 'in the direction of a beam produced by the apparatus' referred to in the appended claims. Movements that are oriented at an angle to Z but according to which a movable portion still approaches towards or recedes away from the target, also qualify as said movements 'in the direction of a beam produced by the apparatus'.

The advantages obtained by the accessory holder of the invention are related to the efficiency of operating the particle beam installation: irradiation with and without an accessory in the beam path can be effected with the accessory remaining attached to the holder, and without interrupting the treatment or at least without manually adjusting the accessory. At the same time, irradiations can be performed with the accessory at various positions in the direction of the beam path. For example, when shallow target volumes, i.e. target volumes close to the skin surface need to be treated, a range shifter needs to be installed in the beam line in order to further reduce the minimum energy of the particle therapy apparatus. For example if the minimum energy of the particle therapy apparatus corresponds to a depth in the patient of 5 cm, and shallow tumours close to the skin surface need to be treated, then such a range shifter needs to be used to reduce the penetration depth of the beam with a few cm. With the accessory holder according to the invention, a standard range shifter can be installed in the accessory holder and when a treatment requires the range shifting, the range shifter can be inserted when needed. With the motion of the second movable portion being automated, this insert or extraction of a range shifter can be done without manual intervention of the radiotherapist. The motion can be actuated either from a control in the treatment room or from a control outside the treatment room.

Figure 3:
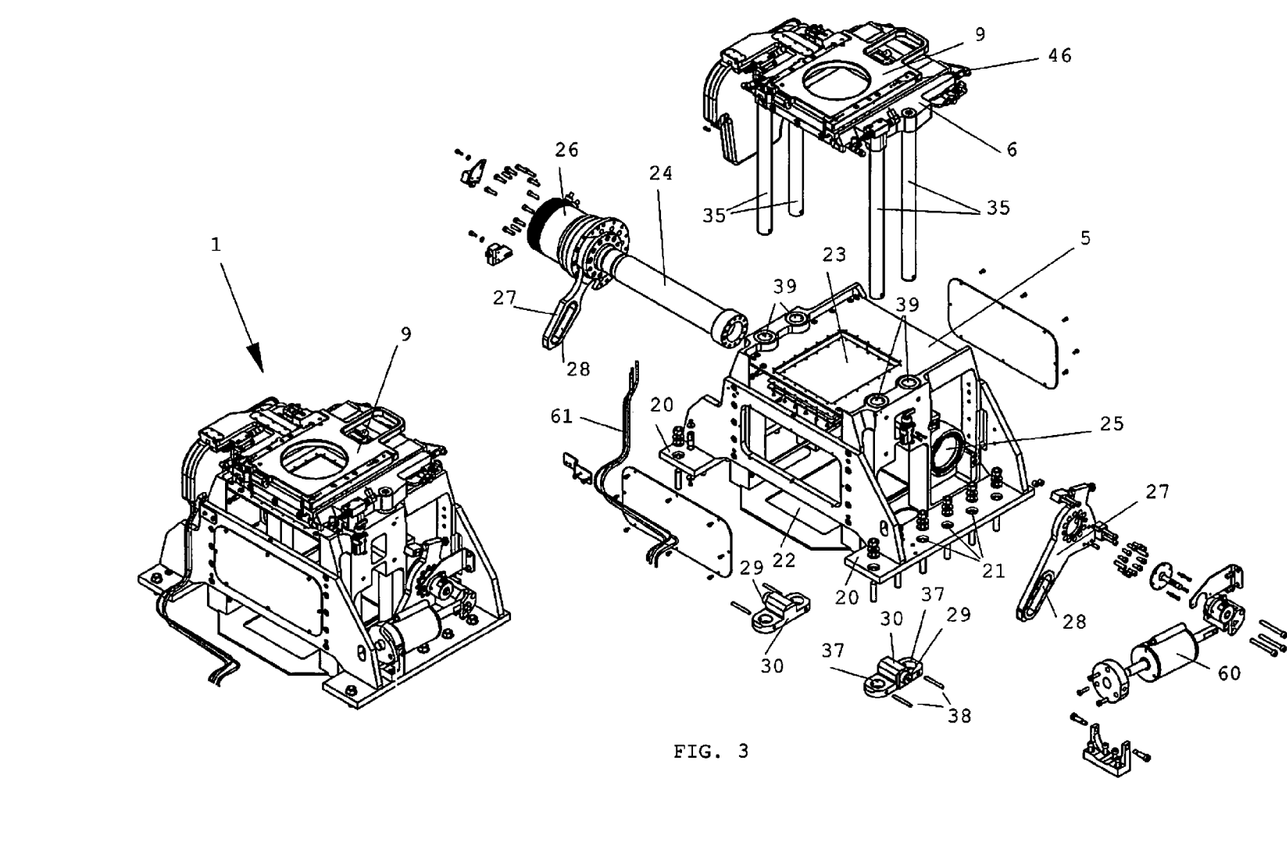
FIG. 3 shows a 3D view and exploded view of an accessory holder according to the first embodiment including all details of the respective displacement mechanisms included in the accessory holder.
Figure 4A:
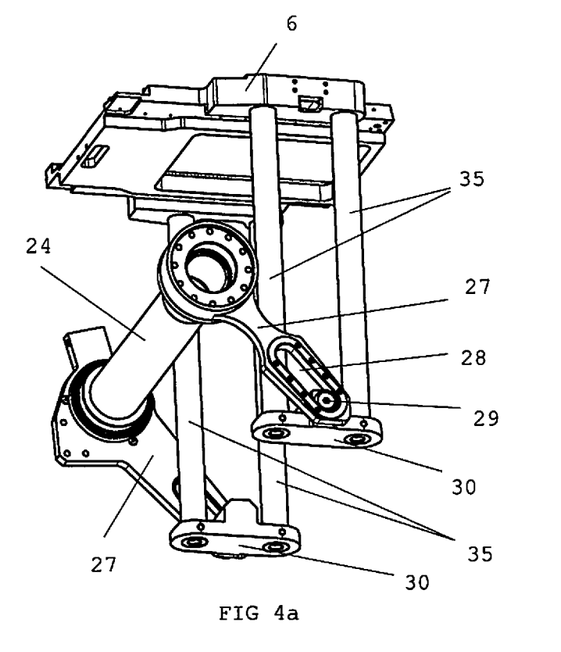
FIGS. 4a and 4b show a detail of one of the displacement mechanisms in an accessory holder according to the embodiment of FIG. 3.
Figure 4B:
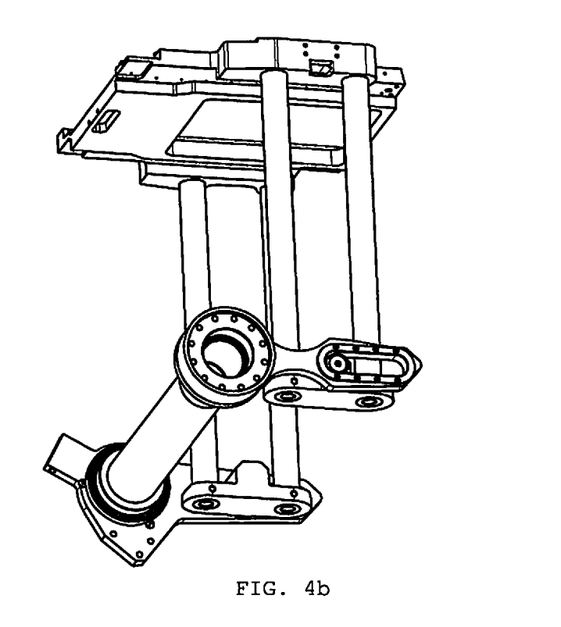
Figure 5A:
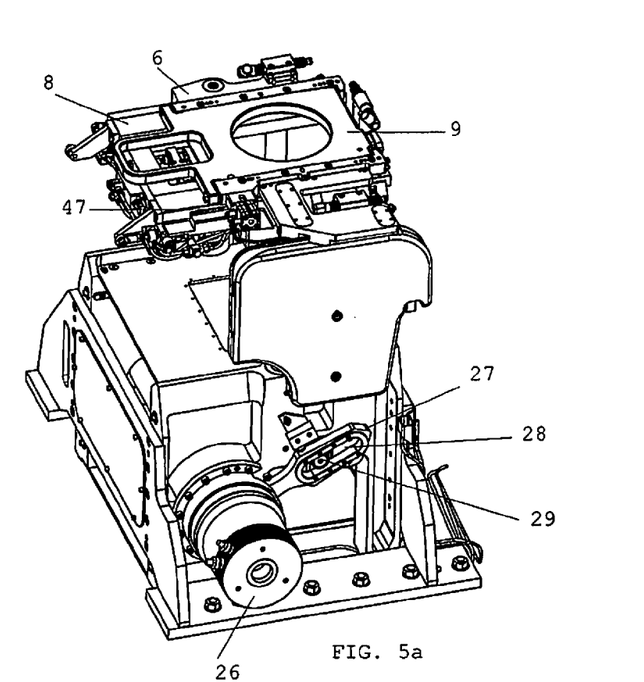
FIGS. 5a and 5b show the accessory holder of FIG. 3 with the accessory holding drawer placed respectively in the beam path and fully extracted out of the beam path.
Figure 5B:
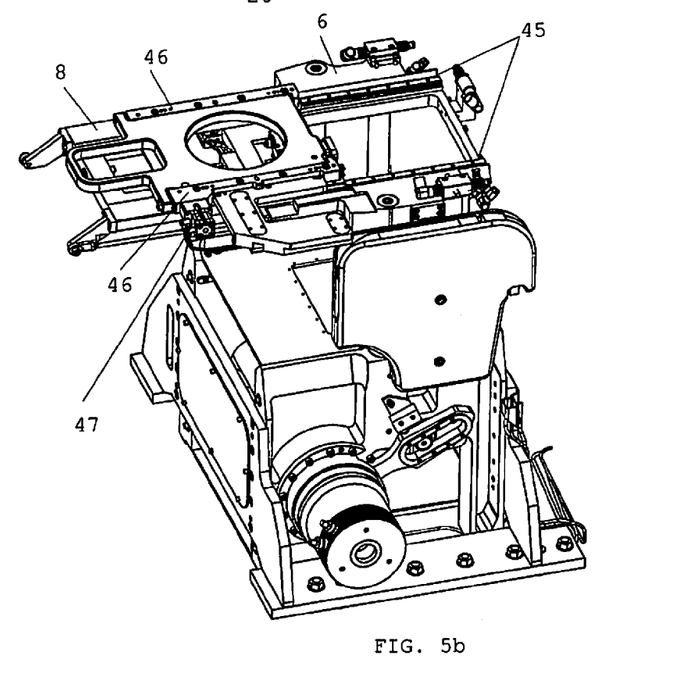

In FIGS. 3, 4 and 5, a detailed view is shown of an accessory holder for a PBS nozzle according to a specific embodiment working according to the principle of FIG. 1. FIG. 3 shows a 3D view of the accessory holder according to the invention, holding a circle-shaped aperture accessory 9. The blow-up view illustrates the main components. The base portion 5 is a box-shaped piece assembled from machined plates (e.g. steel). Support plates are provided with holes 21 through which the base portion 5 can be bolted to the face of the nozzle (not shown). Bottom and top openings 22 and 23 are provided for allowing the passage of the particle beam. An axle 24, rotatable with respect to the base portion 5, passes through holes 25 in two opposite side walls of the base portion. The axle is eccentrically placed in the base portion, i.e. it is located laterally with respect to the base portion's center plane perpendicular to said opposite walls, in a position so that it is unable to block the beams passing through the openings 22/23.

The axle's rotation in the two rotation directions is driven by an electric motor 26. Fixed to the axle 24, i.e. rotating together with the axle, two actuator arms 27 are mounted, one on each side of the base portion 5. The actuator arms have elongate openings 28, configured to receive a cylindrical protrusion 29 of a support piece 30. To each of the two support pieces 30, a pair of cylindrical rods 35 is connected by inserting the rods into openings 37 of the support pieces and securing them by securing pins 38. The rods 35 are inserted in openings 39 provided in the upper surface of the base portion 5. The shape and dimensions of the elongate openings 28 and the protrusions 29 as well as their respective materials are selected such that rotation of the axle 24 actuates a linear movement of the rods 35 guided by the holes 39, through the movement of the protrusions 29 inside the elongate openings 28. The two extreme positions of this mechanism are shown in more detail in FIGS. 4a and 4b. The shape of the two actuator arms 27 is different in this embodiment, as these arms have been designed to actuate the exact same movement of the rods 35, taking into account a torsional deformation of the axle 24.

The set of four rods 35 supports the first movable portion 6 which is in this embodiment a flat rectangular frame attached to the end of the rods 35. The second movable portion is in this embodiment a slidable drawer 8 configured to move perpendicularly to the rods 35, driven by a pneumatic drive mechanism. FIGS. 5a and 5b show the two extreme positions of the drawer 8. It can be seen that the drawer is guided by lateral guides or rails 45 on the first movable portion 6.

The drawer 8 comprises a rectangular receiving area delimited by side beams 46, into which the accessory can be inserted by sliding the accessory into said area. Pneumatically operated locking pins 47 are provided for maintaining the accessory in a fixed position with respect to the drawer 8. So in this embodiment, the interface is not a separate piece, but it is incorporated in the drawer itself (the second movable portion referred to in the claims). The element that is inserted into the drawer can be the aperture piece 9 shown in the drawings, or it can be a support element such as a tray or a snout, that is itself designed to carry the accessory, e.g. a range shifter. The support element is then designed to fit into the drawer, in the same way that is shown for the aperture piece 9.

According to the specific embodiment shown in FIGS. 3, 4 and 5, the drawer can move along the central beam direction away from or towards the nozzle over a distance of maximum 25 cm. Preferably, the first displacement means for moving the accessory interface in a first direction allow for movement of the interface over a distance of more than 10 cm. More preferably, the first displacement means allow for movement of the interface over a distance of more than 20 cm.

Other elements that are visible in FIGS. 3 and 5, but which are not essential to the general concept of the invention are the following: a brake 60 for stopping the movement of the rods 35, pneumatic supply lines 61.

Figure 6A:
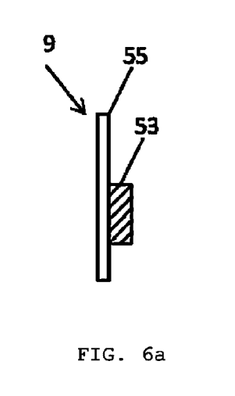
FIG. 6 shows an accessory holder holding a tray that is itself holding an accessory.
Figure 6B:
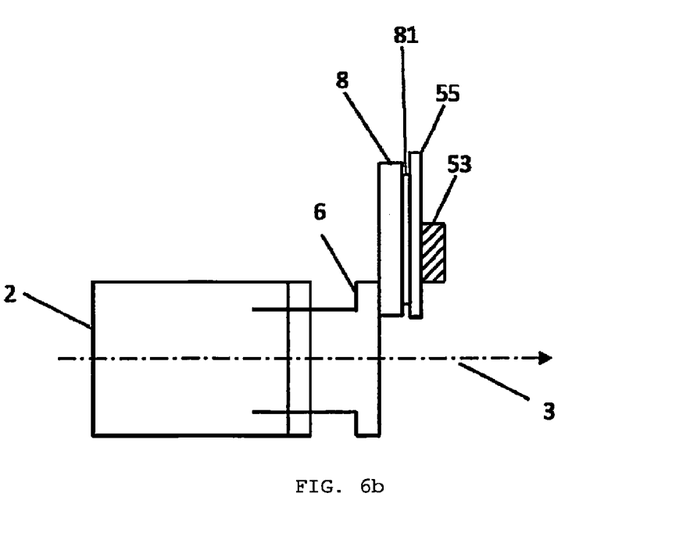

As stated, the accessory 9 can be an aperture, a range shifter, a ridge filter, a range compensator or any other type accessory. What is drawn as the accessory 9 in FIGS. 1 and 2 can also be itself a means for holding other accessories such as an aperture piece, range shifter etc. FIG. 6 illustrates an embodiment wherein the accessory 9 comprises a tray 55 configured for fitting in a slot of the interface 81 as illustrated in FIG. 6a and FIG. 6b. On the tray 55, a range shifter 53 or another accessory such as a ridge filter or an aperture can be attached. FIG. 6b shows the tray 55 attached to the interface 81 of the accessory holder 1 whereby, in this illustration, the interface 81 of the accessory holder 1 is in a position out of a central beam path 3. In this example, the tray 55 fulfils the role of an accessory holding element.

Figures 7A, 7B, 7C:
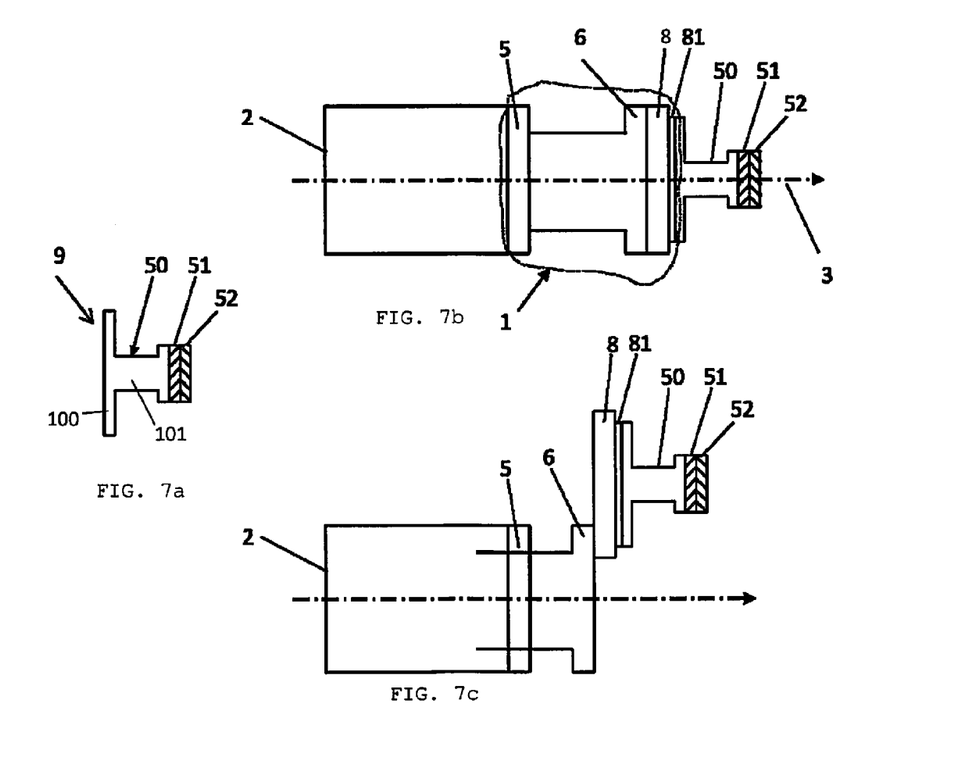
FIG. 7 shows an accessory holder holding a snout that is itself holding two accessories.
Figure 8:
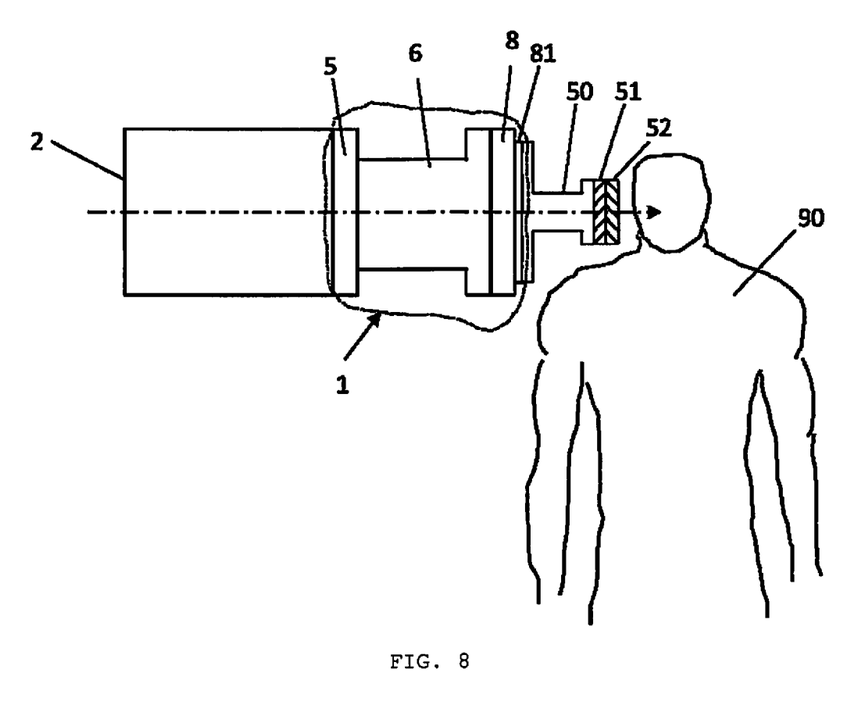
FIG. 8 shows the positioning of the accessory holder equipped with a snout, with respect to a patient.

In the embodiment illustrated in FIG. 7, the accessory 9 comprises a snout 50 attachable to the interface 81 of the second movable portion 8. The snout 50 can for example be configured for fitting in a slot of the interface 81. The snout 50 itself is a structure having a base 100 and a protruding portion 101 provided at the end with a plurality of slots or other means into which accessories can be fitted. The snout thus allows to hold one or more accessories such as an aperture or a range compensator or a ridge filter or a range shifter. The snout 50 can for example comprise two slots (not shown on the figure) for receiving two accessories at the same time, for example an aperture and a range compensator. FIG. 7a shows a snout 55 holding two accessories 51 and 52 which can for example be an aperture and a range compensator. FIG. 7b shows the accessory holder 1 attached to a nozzle 2 whereby the snout 55 is positioned in a central beam path 3. FIG. 7c shows the same snout 55 as in FIG. 7b but in a geometry whereby the snout is positioned out of a central beam path 3 using the second movable portion 8 and whereby the snout is located closer to the nozzle when compared to FIG. 7b by using the motion of the first movable portion 6. The advantage of attaching a snout 50 to the accessory holder 1 is that accessories (aperture, range compensator, ridge filter, range shifter) can be brought very close to the patient as illustrated in FIG. 8. For example, for a head treatment, a snout 50 with a small diameter is used so that the shoulder of the patient 90 is not in collision with the snout. Typically, a library of different snouts having different diameters will be available for the particle therapy apparatus. For example a library of three different snouts can comprise a first snout for holding circular accessories having a diameter up to 12 cm, a second snout for holding circular accessories having a diameter up to 20 cm and a third snout for holding accessories having a rectangular shape of for example 28 cm×38 cm. On each snout 50, corresponding accessories 51,52 of a given maximum diameter can be mounted. Depending on the size of the target volume to be treated, the adequate size of the snout and corresponding accessories can be selected. In this example, the snout 50 fulfils the role of an accessory holding element.

Other displacement mechanisms may be used instead of the ones shown in the embodiment of FIGS. 3 to 5, for example a system comprising an extendable portion 6 that is movable on a set of rails, as it is known for supporting and moving a collimator closer to or away from the target in a double scattering installation. According to an embodiment however, the displacement mechanism for movement in the direction of the beam does not comprise nor consist of a bellows-type mechanism. The mechanism comprising the actuator arms 27 and support rods 35 has however a specific advantage in that it is very compact in the direction of the beam. Given that the accessory holder must be able to further support and manipulate the second movable portion 8, this provides a maximum of movement space for the accessory.

The invention therefore finds its primary use in PBS scanning installations, wherein a variety of accessories, including an aperture piece for, for example, sparing organs at risk, can be positioned with the holder of the invention.

While the invention has been illustrated and described in detail in the drawings and foregoing description, such illustration and description are to be considered illustrative or exemplary and not restrictive. Other variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The foregoing description details certain embodiments of the invention. It will be appreciated, however, that no matter how detailed the foregoing appears in text, the invention may be practiced in many ways, and is therefore not limited to the embodiments disclosed. It should be noted that the use of particular terminology when describing certain features or aspects of the invention should not be taken to imply that the terminology is being re-defined herein to be restricted to include any specific characteristics of the features or aspects of the invention with which that terminology is associated.

The invention claimed is:

1. A holder for a treatment accessory for use with a particle beam treatment apparatus having a nozzle for delivering, along a first direction, a beam to a target, the holder being coupled to the nozzle and comprising:

an interface comprising an opening for receiving the treatment accessory and a locking mechanism for locking the treatment accessory in the opening, a first displacer configured for moving the interface in the first direction, so that the accessory, while being held by the interface, is moved away from or towards the nozzle in the first direction of the beam produced by the particle beam treatment apparatus, and a second displacer configured for moving the interface in a second direction, so that the treatment accessory, while being held by the interface, is moved into or out of the path of a beam produced by the particle beam treatment apparatus.

2. The holder according to claim 1, wherein:

the first displacer comprises a first movable portion configured to move in the first direction with respect to the nozzle;

the second displacer comprises a second movable portion configured to move in the second direction with respect to the first movable portion; and the interface is integrated with the second movable portion.

3. The holder according to claim 1, wherein:

the second displacer comprises a second movable portion configured to move in the second direction with respect to the nozzle;

the first displacer comprises a first movable portion configured to move in the first direction with respect to the second movable portion; and the first movable portion comprises the interface.

4. The holder according to claim 3, wherein the movement in the second direction, into or out of the path of the beam, is a linear translational movement.

5. The holder according to claim 2, wherein the first displacer further comprises a rotatable axle including actuator arms and adapted to move the first movable portion along the first direction away from or towards the nozzle.

6. The holder according to claim 5, wherein:

the second movable portion comprises a slidable drawer configured to slide back and forth in the second direction; and the drawer comprises the interface.

7. The holder according to claim 6, further comprising:
a base portion connectable to the nozzle;
wherein the first or second displacer is mounted on the base portion.

8. The holder according to claim 6, further comprising:
a base portion connectable to the nozzle,
wherein the first or second displacer is mounted on the base portion, and the first displacer further comprises:
a plurality of support pieces; and
a plurality of support rods attached at one end to the support pieces and support the first movable portion at the other end;
wherein the base portion includes guide holes into which the support rods are inserted, and
wherein the actuator arms include elongate openings adapted to slidably receive the ends of the support pieces such that rotation of the actuator arms actuates a linear movement of the support rods.

9. The holder according to claim 1, wherein the first and the second displacer are motorized and actuatable from a distance.

10. The holder according to claim 9, wherein the first or the second displacer comprises one of an electrical or pneumatic drive.

11. The holder according to claim 1, wherein the first direction is the direction of a first linear path, and wherein the second direction is the direction of a second linear path perpendicular to the first linear path.

12. A particle beam apparatus comprising:
an irradiation source; and
a nozzle,
wherein a holder according claim 1 is mounted on or integrated with the nozzle.

13. The apparatus according to claim 12, further comprising a particle beam scanning device for scanning a particle beam over a target.

14. The apparatus according to claim 13, further comprising:
a tray attachable to the holder and configured for holding at least one of an aperture, a range compensator, a ridge filter, or a range shifter.

15. A method for positioning a treatment accessory in a particle beam treatment apparatus, comprising:
inserting and securing the treatment accessory in an interface of a holder; and
moving the treatment accessory along at least one of a first or a second direction,
wherein:
the interface comprises a slot for inserting and removing the treatment accessory and a locking mechanism for locking the accessory, and
wherein the holder comprises:
a first displacer adapted for moving the interface in a first direction, so that the treatment accessory, while being held by the interface, is moved away from or towards the nozzle in the direction of a beam produced by the particle beam treatment apparatus, and
a second displacer adapted for moving the interface in a second direction so that the treatment accessory, while being held by the interface, is moved into or out of the path of a beam produced by the particle beam treatment apparatus,
wherein movement of the treatment accessory brings the treatment accessory in a predefined position with respect to a target; and
the treatment accessory remains inserted and secured in the interface during movement of the treatment accessory.

16. The method according to claim 15, wherein the movements of the treatment accessory are actuated by an automated drive.

17. The method according to claim 16, wherein the treatment accessory includes at least one of an aperture piece; a range shifter; a ridge filter for use with a Pencil Beam Scanning nozzle; or a holder for holding an aperture piece, range shifter, or ridge filter.

* * * * *